(12) United States Patent
O'Neil

(10) Patent No.: US 9,181,303 B2
(45) Date of Patent: Nov. 10, 2015

(54) TREATMENT OF BACTERIAL INFECTIONS WITH CYCLIC ANTIMICROBIAL PEPTIDES

(71) Applicant: NOVABIOTICS LIMITED, Aberdeen (GB)

(72) Inventor: Deborah O'Neil, Inverurie (GB)

(73) Assignee: NovaBiotics Limited, Aberdeen (GB)

( * ) Notice: Subject to any disclaimer, the term of this patent is extended or adjusted under 35 U.S.C. 154(b) by 0 days.

(21) Appl. No.: 14/311,093

(22) Filed: Jun. 20, 2014

(65) Prior Publication Data

US 2014/0303071 A1    Oct. 9, 2014

Related U.S. Application Data

(60) Continuation-in-part of application No. 13/592,246, filed on Aug. 22, 2012, now Pat. No. 8,785,375, which is a division of application No. 12/158,945, filed as application No. PCT/GB2006/004890 on Dec. 21, 2006, now Pat. No. 8,324,154.

(60) Provisional application No. 60/776,505, filed on Feb. 24, 2006.

(30) Foreign Application Priority Data

Dec. 22, 2005    (GB) .................................. 0526120.1

(51) Int. Cl.
| | | |
|---|---|---|
| *A61K 38/12* | (2006.01) | |
| *C07K 7/64* | (2006.01) | |
| *C07K 14/47* | (2006.01) | |
| *A61K 38/00* | (2006.01) | |

(52) U.S. Cl.
CPC ............... *C07K 7/64* (2013.01); *C07K 14/4723* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,916,872 | A | * | 6/1999 | Chang et al. .................... 514/2.6 |
| 6,001,961 | A | | 12/1999 | Jonczyk et al. |
| 6,156,730 | A | * | 12/2000 | Little et al. ...................... 514/3.3 |
| 6,951,652 | B2 | * | 10/2005 | Porro ........................... 424/234.1 |
| 2003/0087827 | A1 | | 5/2003 | Lindberg et al. |
| 2005/0107289 | A1 | * | 5/2005 | Ghadiri et al. .................... 514/9 |
| 2006/0128614 | A1 | * | 6/2006 | Cheng et al. ..................... 514/9 |

FOREIGN PATENT DOCUMENTS

| | | | |
|---|---|---|---|
| WO | 95/03327 | A2 | 2/1995 |
| WO | 2004/050685 | A2 | 6/2004 |
| WO | WO2004/050685 | * | 6/2004 |
| WO | 2006/018652 | A2 | 2/2006 |

OTHER PUBLICATIONS

Oren, Ziv et al., "Cyclization of a Cytolytic Amphipathic a-Helical Peptide and Its Diastereomer: Effect on Structure, Interaction with Model Membranes, and Biological Function," Biochemistry 2000, vol. 39, pp. 6103-6114 (Apr. 2000).

\* cited by examiner

*Primary Examiner* — Elly-Gerald Stoica
(74) *Attorney, Agent, or Firm* — Janet Sleath; Speckman Law Group PLLC

(57) ABSTRACT

The present invention relates to cyclic cationic peptides and their use in the treatment of microbial infections.

10 Claims, No Drawings

TREATMENT OF BACTERIAL INFECTIONS WITH CYCLIC ANTIMICROBIAL PEPTIDES

REFERENCE TO RELATED APPLICATIONS

This application is a continuation-in-part of U.S. patent application Ser. No. 13/592,246, filed Aug. 22, 2012, which is a divisional of U.S. patent application Ser. No. 12/158,945, filed Aug. 15, 2008, which is the US national phase entry of PCT patent application no. PCT/GB2006/04890, filed Dec. 21, 2006, which claims priority to U.S. provisional application No. 60/776,505, filed Feb. 24, 2006 and United Kingdom patent application no. 0526120.1, filed Dec. 22, 2005.

FIELD OF THE INVENTION

The present invention relates to cyclic cationic peptides and their use in the treatment of microbial infections.

BACKGROUND TO THE INVENTION

Antimicrobial peptides (AMP) form the cornerstone of eukaryotic immunity and provide a first line of defense against breach of the skin and mucosal surfaces by micro-organisms. Examples of natural AMP include the defensin and cathelicidin families of peptides. These AMP are heterogeneous in length, sequence and structure, but common to most is their small size, net cationic charge and amphipathic structure. Small, cationic antimicrobial peptides have also been isolated from many bacteria, fungi, plants, invertebrates and vertebrates and would therefore appear also to play a role in prokaryotic defenses.

Natural AMP exhibit broad-spectrum activity against Gram-positive and Gram-negative bacteria, yeasts, fungi and enveloped viruses. Microbial pathogens do not seem to acquire resistance to these cationic peptides and as such, AMP have been conserved as a vital innate immune host defense molecules through millennia of evolution. It is not surprising therefore that AMP have been implicated as potential targets for therapeutics for a wide range of infections. However, the fact that they are technically challenging and costly to produce in recombinant systems and have potent chemotactic and inflammatory biological functions rules out natural AMP forms for use as therapeutics.

In our co-pending application we have shown that linear peptides rich in certain basic residues such as lysine or arginine possess antimicrobial activity, and, in particular, anti-fungal activity. There remains, however, a need for further agents that can be used in the treatment or prevention of microbial infections.

STATEMENTS OF THE INVENTION

According to a first aspect of the invention, there is provided a peptide comprising from 2 to about 200 D and/or L amino acids, which may be the same or different, wherein the amino acids are selected from the group consisting of hydrophobic amino acids and/or cationic amino acids, and wherein the peptide is cyclic. The cyclic peptide may comprise 3 to about 100 D and/or L amino acids, for example 3 to 50 amino acids D and/or L amino acids including 4 to about 50 D and/or L-amino acids.

The peptides of the invention are useful in the treatment or prevention of microbial infections.

The cyclic peptides of the invention are desirable as a therapeutic as they are highly effective, proteolytically stable, substantially salt insensitive, not hepatotoxic, non-haemolytic and easy to synthesize.

The cationic charge of the peptides of the invention is believed to facilitate the association of the peptide with the polar head-groups of microbial membranes. Stabilization of the charged groups in a more dense confirmation by cyclisation is believed to enhance this attraction thereby increasing the antimicrobial potency of the peptides.

In a further aspect of the invention there is provided a peptide comprising amino acids according to the formula I:

$$((X)_l(Y)_m)_n \qquad (I)$$

wherein l and m are integers from 0 to 10 such that both l and m are not 0; n is an integer from 1 to 10; X and Y, which may be the same or different, are an amino acid selected from the group consisting of hydrophobic amino acids and/or cationic amino acids and wherein the peptide is cyclic, for use as a pharmaceutical.

The peptide may comprise from 2 to 50 amino acids, for example 3, 4, 5, 6, or 7 up to 50 amino acids, including 3, 4, 5, 6, or 7 up to 10, 15, 20, 25, 30, 35, 40, 45 or 50 amino acids.

In a preferred aspect of the invention the peptide comprises 2 to 15 amino acids, for example 3 to 15 amino acids. Preferably still the peptide comprises 5 to 13 amino acids. Yet further preferred are peptides comprising 3 to 7 amino acids, for example 7 amino acids.

As known to the skilled person, amino acids can be placed into different classes depending primarily upon the chemical and physical properties of the amino acid side chain. For example, some amino acids are generally considered to be hydrophilic or polar amino acids and others are considered to be hydrophobic or non-polar amino acids. Hydrophobic amino acid may be selected from the group of hydrophobic amino acids consisting of glycine, leucine phenylalanine, proline, alanine, tryptophan, valine, isoleucine, methionine, tyrosine and threonine; cationic amino acids may be selected from the group consisting of ornithine, histidine, arginine and lysine. As used herein, the terms "hydrophobic" and "cationic" may refer to amino acids having a hydrophobicity that is greater than or equal to −1.10 and/or a net charge that is greater than or equal to 0 as described in Fauchere and Pliska Eur. J. Med Chem. 10:39 (1983). A hydrophobic or non-polar amino acid may also refer to an amino acid having a side chain that is uncharged at physiological pH, is not polar and that is generally repelled by aqueous solution. The amino acids may be naturally occurring or synthetic.

In a preferred aspect of the invention, X and/or Y are cationic amino acids selected from the group consisting of histidine, ornithine arginine and lysine. Preferably still X and/or Y are arginine or lysine.

X and/or Y may optical isomers of a hydrophobic or cationic amino acid as defined herein for example D or L-amino acids. Preferably X and/or Y are D-amino acids.

In a preferred aspect of the invention, the peptide of formula (I) consists of at least 90%, for example at least 95% such as 97-99% or even 100%, of D-amino acids.

In a preferred aspect of the invention, the peptide of formula (I) consists of at least 90%, for example at least 95% such as 97-99% or even 100%, of L-amino acids.

The invention also includes known isomers (structural, stereo-, conformational and configurational), peptidomimetics, structural analogues of the above amino acids, and those modified either naturally (e.g. post-translational modification) or chemically, including, but not exclusively, phosphorylation, glycosylation, sulfonylation and/or hydroxylation.

In general, the peptide of the invention does not include the amino acids aspartic acid, glutamic acid, asparagine, glutamine or serine, but certain peptides of the invention may have activity even though these amino acids are present.

In a further preferred aspect, X and Y are the same. Preferably still X and Y are the same and are lysine or arginine.

In the peptide of formula (I) l and m may be 1, 2, 3, 4, 5, 6, 7, 8, 9 or 10 and n may be 1, 2, 3, 4, 5, 6, 7, 8, 9 or 10.

In the peptide of formula (I) l may be 1, n may be 1 and m may be between 4 and 9, for example, m may be 3, 4, 5, 6, 7, 8 or 9.

In the peptide of formula (I) l, n and/or m may be between 1 and 5, for example, 1, 2, 3, 4 or 5.

In the peptide of formula (I) l and m may be an integer between 0 and 7 and n may be an integer between 1 and 10.

In the peptide of formula (I) l and m may be 0, 1 or 2 and n may be an integer between 1 and 10.

In the peptide of formula (I) X and Y may be the same, l may be 0, m may be 1 and n may be 3, 4, 5, 6, 7, 8, 9 or 10.

In the peptide of formula (I) X and Y may be the same, l and m may be 1 and n may be 2, 3, 4 or 5.

In the peptide of formula (I) X and Y may be the same, l may be 1, m may be 2 and n may be 1, 2, 3 or 4.

In the peptide of formula (I) X and Y may be the same, l and m may be 2 and n may be 1, 2, 3 or 4.

In a further aspect of the invention there is provided a cyclic peptide comprising amino acids according to the formula II:

$(X)_n$                                                        (II)

wherein X and n are as described herein. Preferably X is lysine, arginine or ornithine. Preferably n is an integer between 3 and 15.

In one embodiment of the invention X is arginine.

In an alternative embodiment of the invention X is lysine.

In a yet alternative embodiment of the invention X is ornithine.

The peptides of the invention may comprise one or more cysteine residues, for example up to 6 cysteine residues, such as 1, 2, 3, 4, 5 or 6 cysteine residues.

In addition, the amino acid sequence of the peptide can be modified so as to result in a peptide variant that includes the substitution of at least one amino acid residue in the peptide for another amino acid residue, including substitutions that utilize the D rather than L form.

One or more of the residues of the peptide can be exchanged for another to alter, enhance or preserve the biological activity of the peptide. Such a variant can have, for example, at least about 10% of the biological activity of the corresponding non-variant peptide. Conservative amino acids are often utilized, i.e. substitutions of amino acids with similar chemical and physical properties as described above. Hence, for example, conservative amino acid substitutions may involve exchanging lysine for arginine, ornithine or histidine; or exchanging arginine for lysine or isoleucine, ornithine for histidine; or exchanging one hydrophobic amino acid for another. After the substitutions are introduced, the variants are screened for biological activity.

The term "peptide" as used herein means, in general terms, a plurality of amino acid residues joined together by peptide bonds. It is used interchangeably and means the same as polypeptide and protein.

In one embodiment of the invention, the cyclic peptide is selected from the group consisting of:
K-K-K-K-K-K; and
R-R-R-R-R-R.

The peptides of the invention generally are synthetic peptides. The peptides may be isolated, purified peptides or variants thereof, which can be synthesized in vitro, for example, by a solid phase peptide synthetic method, by enzyme catalyzed peptide synthesis or with the aid of recombinant DNA technology.

In a further aspect of the invention there is provided a process for the preparation of a peptide according to the invention, the process comprising cyclizing a peptide of formula (I) or (II) by reaction of the peptide with a coupling agent.

The coupling agent may be any agent capable of forming a peptide bond between the two terminal (C and N terminal) amino acid residues of the peptide when in its linear form, for example, between two amino acid backbones or side chains. The choice of coupling agent can influence the efficiency of coupling and hence the yield of the cyclic peptide. Examples of coupling agents useful in the process of the invention is shown in Table 1 although the skilled person will be aware of other known coupling agents that are also useful in the invention. Preferably the coupling agent is HATU-O-(7-Azabenzotriazol-1-yl)-N,N,N',N'-tetramethyluroniumhexafluorophosphate.

Preferably the reaction between the peptide and the coupling agent takes place in in the presence of a base. The base may include, but is not limited to, n-methylmorpholine (NMM) or diisopropyl-ethylamine (DIEA). Preferably the reaction takes place at alkaline pH, for example between pH 8.5-9. The peptide may be modified to include a protecting group prior to its reaction with the coupling agent. Protecting groups may include Pbf (2,2,4,6,7-pentamethyl-dihydrobenzofuran-5-sulfonyl), tBu (t-butyl-ether), Mtr (methoxytrimethyl-benzene sulfonyl), Pmc (2,2,5,7,8-pentamethyl-chroman-6-sulfonyl chloride), Mbh (4,4-dimethyloxybenzylhydride), Tmob (2,4,6-trimethoxybenzyl), Aloc (allyloxy-carbonyl), Fmoc (9-fluorenylmethoxycarbonyl) and Boc (t-butyloxycarbonyl). Following reaction with the coupling agent, the protecting group may be removed by cleavage of the protecting group under mild acid conditions, for example in the presence of a solution of trifluoracetic acid (TFA).

During backbone cyclization of peptide, the peptide at the C-terminal of the linear peptide is exposed to an activating group of the coupling agent and as the reaction proceeds a keto-enol intermediate is produced at the alpha carbon of this amino acid. The enol (or alkenol) intermediate can therefore lead to the production of two enantiomers when the activating group is removed from the adjacent carbon and a peptide bond is formed. This racemization i.e. the formation of the respective enantiomers of the individual amino acid (for example dextrorotatory and levorotatory forms (i.e. d and l isomers respectively)) and production of diastereomers of the peptide as a whole, can occur at the site of cyclisation upon activation by the coupling agent used. Since it is desirable for the peptides of the invention to be enantiomerically pure, production of undesirable diastereomers should be reduced or prevented. In order to reduce or prevent this production of diastereomers, and produce a diastereometrically pure peptide, the peptide of the invention may be modified to include an achiral moiety that prevents racemization of the peptide during cyclisation.

Thus in a further preferred aspect of the invention the peptide of the invention, or the peptide defined in the process of the invention, is modified to include a moiety that prevents the formation of peptide diastereomers during cyclisation. As used herein a "racemic peptide" is one that contains quantities (typically equal quantities) of the respective optical isomers, for example dextrorotatory and levorotatory forms (i.e. d and l isomers respectively), of the amino acid at the C-terminal of the peptide prior to cyclisation of the peptide. The moiety introduced into the peptide is generally an achiral amino acid which may be a naturally occurring amino acid or an amino acid analogue. The achiral amino acid may be selected from the group consisting of glycine, β-alanine, 3-aminopropanoic acid, 4-amino butyric acid, 5-aminopentanoic acid and 6-aminohexanoic acid. In one embodiment of the invention the peptide is modified at the C-terminal to include an achiral amino acid, for example glycine.

As well as modifying the peptide of the invention to include a moiety, as defined herein, at the C-terminal, the ratio of the two enantiomers formed during cyclisation of the peptide is dependent on several factors such as the solvent used, incubation time and temperature during cyclization (i.e. reaction with the coupling agent) and the activating group used to facilitate the cyclisation.

The present invention further relates to cyclized peptides obtainable by the process of the invention.

In one embodiment of the invention, the cyclic peptide comprises an amino acid sequence selected from the group consisting of:

K-K-K-K-K-K-K;
R-R-R-R-R-R-R;
O-O-O-O-O-O-O;
DR-DR-DR-DR-DR-DR-DR;
DO-DO-DO-DO-DO-DO-DO; and
DK-DK-DK-DK-DK-DK.

To identify active peptides that have little or no undesired toxicity for mammalian cells, individual peptides, or libraries of peptides, can be made and the individual peptides or peptides from those libraries can be screened for antimicrobial activity and toxicity, including, but not limited to, antifungal, antibacterial, antiviral, antiprotozoal, anti-parasitic activity and toxicity.

The peptides of the invention can exist in different forms, such as free acids, free bases, esters and other prodrugs, salts and tautomers, for example, and the invention includes all variant forms of the compounds.

Thus, the invention encompasses the salt or pro-drug of a peptide or peptide variant of the invention.

The peptide of the invention may be administered in the form of a pharmaceutically acceptable salt. The pharmaceutically acceptable salts of the present invention can be synthesized from the parent peptide which contains a basic or acidic moiety by conventional chemical methods. Generally, such salts can be prepared by reacting the free acid or base forms of the peptide with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., US, 1985, p. 1418, the disclosure of which is hereby incorporated by reference; see also Stahl et al, Eds, "*Handbook of Pharmaceutical Salts Properties Selection and Use*", Verlag Helvetica Chimica Acta and Wiley-VCH, 2002.

The invention thus includes pharmaceutically-acceptable salts of the peptide of the invention wherein the parent compound is modified by making acid or base salts thereof for example the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glutamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Salts of carboxyl groups of a peptide or peptide variant of the invention may be prepared in the usual manner by contacting the peptide with one or more equivalents of a desired base such as, for example, a metallic hydroxide base, e.g. sodium hydroxide; a metal carbonate or bicarbonate such as, for example, sodium carbonate or bicarbonate; or an amine base such as, for example, triethylamine, triethanolamine and the like.

The invention includes prodrugs for the active pharmaceutical species of the described peptide, for example in which one or more functional groups are protected or derivatized but can be converted in vivo to the functional group, as in the case of esters of carboxylic acids convertible in vivo to the free acid, or in the case of protected amines, to the free amino group. The term "prodrug," as used herein, represents in particular structures which are rapidly transformed in vivo to the parent structure, for example, by hydrolysis in blood.

A further aspect of the invention provides a pharmaceutical composition comprising a pharmaceutically effective amount of a peptide of the invention, or two or more different peptides of the invention.

The composition also includes a pharmaceutically acceptable carrier, excipient or diluent. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

The peptide of the invention is useful, inter alia, as an antimicrobial peptide, for example, against bacteria, fungi, yeast, parasites, protozoa and viruses. The term, "antimicrobial peptide" can be used herein to define any peptide that has microbicidal and/or microbistatic activity and encompasses, non-exclusively, any peptide described as having anti-bacterial, anti-fungal, anti-mycotic, anti-parasitic, anti-protozoal, anti-viral, anti-infectious, anti-infective and/or germicidal, algicidal, amoebicidal, microbicidal, bacterici(o)dal, fungicidal, parasiticidal, protozoacidal, protozoicidal properties.

In a preferred aspect, the invention provides the use of a peptide according to the invention in the manufacture of a medicament for treating a microbial infection.

By "microbial infection" is meant an infection caused by a bacterium, parasite, protozoa, virus or fungus including yeast. A "pathogen" is generally defined as any disease-causing organism.

A bacterial pathogen may be derived from a bacterial species selected from the group, but not exclusive to the group, consisting of: *Staphylococcus* spp., e.g. *Staphylococcus aureus* (e.g. *Staphylococcus aureus* NCTC 10442 and *Sta-* phylococcus aureus ATCC25923), *Staphylococcus epidermidis; Chlamydia* spp., e.g. *Chlamydia trachomatis, Chlamydia pneumoniae, Chlamydia psittaci; Enterococcus* spp., e.g. *Enterococcus faecalis; Streptococcus pyogenes; Listeria* spp.; *Pseudomonas* spp.; *Mycobacterium* spp., e.g. *Mycobacterium tuberculosis; Enterobacter* spp.; *Campylobacter* spp.; *Salmonella* spp.; *Streptococcus* spp., e.g. *Streptococcus* Group A or B, *Streptoccocus pneumoniae; Helicobacter* spp., e.g. *Helicobacter pylori; Neisseria* spp., e.g. *Neisseria gonorrhoea, Neisseria meningitidis; Borrelia burgdorferi; Shigella* spp., e.g. *Shigella flexneri; Escherichia coli (E. coli O157:H7 NCTC 12900); Haemophilus* spp., e.g. *Haemophilus influenzae; Francisella tularensis; Bacillus* spp., e.g. *Bacillus anthracis; Clostridia* spp., e.g. *Clostridium botulinum, Clostridium difficile; Yersinia* spp., e.g. *Yersinia pestis; Treponema* spp.; *Burkholderia* spp., e.g. *Burkholderia cepacia, B. mallei, B. pseudomallei;* and *Propionibacterium* spp., e.g. *P. acnes.*

In a preferred use according to the invention the bacterial pathogen is *Staphylococcus aureus* or *E. coli.*

A viral pathogen may be derived from a virus selected from, but not limited to, the group consisting of: Human Immunodeficiency Virus (HIV1 & 2); Human T Cell Leukaemia Virus (HTLV 1 & 2); Ebola virus; human papilloma virus (e.g. HPV-2, HPV-5, HPV-8 HPV-16, HPV-18, HPV-31, HPV-33, HPV-52, HPV-54 and HPV-56); papovavirus; rhinovirus; poliovirus; herpesvirus; adenovirus; Epstein Barr virus; influenza virus; hepatitis B and C viruses; Variola virus; rotavirus; and SARS coronavirus.

A parasitic pathogen may be derived from a parasite selected from, but not limited to, the group consisting of *Trypanosoma* spp. (*Trypanosoma cruzi, Trypansosoma brucei*), *Leishmania* spp., *Giardia* spp., *Trichomonas* spp., *Entamoeba* spp., *Naegleria* spp., *Acanthamoeba* spp., *Schistosoma* spp., *Plasmodium* spp., *Crytosporidium* spp., *Isospora* spp., *Balantidium* spp., *Loa Loa, Ascaris lumbricoides, Dirofilaria immitis,* and *Toxoplasma* ssp., e.g. *Toxoplasma gondii.*

In a preferred use according to the invention the microbial infection is a fungal infection.

A fungal pathogen may be derived from a fungus (including yeast) selected from, but not limited to, the genera *Candida* spp., (e.g. *C. albicans*), *Epidermophyton* spp., *Exophiala* spp., *Microsporum* spp., *Trichophyton* spp., (e.g. *T. rubrum* and *T. interdigitale*), *Tinea* spp., *Aspergillus* spp., *Blastomyces* spp., *Blastoschizomyces* spp., *Coccidioides* spp., *Cryptococcus* spp. (e.g. *Cryptococcus neoformans*), *Histoplasma* spp., *Paracoccidiomyces* spp., *Sporotrix* spp., *Absidia* spp., *Cladophialophora* spp., *Fonsecaea* spp., *Phialophora* spp., *Lacazia* spp., *Arthrographis* spp., *Acremonium* spp., *Actinomadura* spp., *Apophysomyces* spp., *Emmonsia* spp., *Basidiobolus* spp., *Beauveria* spp., *Chrysosporium* spp., *Conidiobolus* spp., *Cunninghamella* spp., *Fusarium* spp., *Geotrichum* spp., *Graphium* spp., *Leptosphaeria* spp., *Malassezia* spp. (e.g *Malassezia Furfur*), *Mucor* spp., *Neotestudina* spp., *Nocardia* spp., *Nocardiopsis* spp., *Paecilomyces* spp., *Phoma* spp., *Piedraia* spp., *Pneumocystis* spp., *Pseudallescheria* spp., *Pyrenochaeta* spp., *Rhizomucor* spp., *Rhizopus* spp., *Rhodotorula* spp., *Saccharomyces* spp., *Scedosporium* spp., *Scopulariopsis* spp., *Sporobolomyces* spp., *Syncephalastrum* spp., *Trichoderma* spp., *Trichosporon* spp., *Uloocladium* spp., *Ustilago* spp., *Verticillium* spp., and *Wangiella* spp.

In a preferred use according to the invention the fungal pathogen is of the genera *Trichophyton* spp. or *Cryptococcus* spp. For example the fungal pathogen may be *Trichophyton rubrum, Trichophyton interdigitale* or *Cryptococcus neoformans.*

The fungal infection may be a systemic, topical, subcutaneous, cutaneous or mucosal infection.

Topical fungal infections of the nails and skin are generally caused by dermatophytes although some non-dermatophytes such as yeast can also cause skin infections. The dermatophyte infection may include a Tinea infection for example *Tinea barbae* (beard), *Tinea capitis* (head), *Tinea corporis* (body), *Tinea cruris* (groin), *Tinea faciei* (face), *Tinea manuum* (hand), *Tinea pedis* (foot) *Tinea unguium* (nail), *Tinea* (Pityriasis) *versicolor, Tinea incognito* or *Tinea nigra.* The infection may be derived from fungi of the genera *Epidermophyton, Microsporum* or *Trichophyton* spp. (e.g. *T. rubrum* and *T. interdigitale*).

The dermatophytic infection may be an infection of the skin, lamina, stratum corneum, nails (fingernails and toenails) or hair. Of particular mention are dermatophytic infections caused by a dermatophyte of the genera *Trichophyton, Epidermophyton* or *Microsporum.* Exemplary dermatophytes include *Epidermophyton floccosum, Microsporum canis, Microsporum audouinii, Microsporum gypseum, Microsporum nanum, Microsporum ferrugineum, Microsporum distortum, Microsporum fulvum, Trichophyton rubrum, Trichophyton mentagrophytes* var. *interdigitale, Trichophyton mentagrophytes* var. *nodulare, Trichophyton tonsurans, Trichophyton soudanese, Trichophyton violaceum, Trichophyton megnini, Trichophyton schoenlenii, Trichophyton gallinae, Trichophyton krajdenii, Trichophyton yaoundei, Trichophyton equinum, Trichophyton erinacei* and *Trichophyton verrucosum.*

In a particular embodiment of the invention, the dermatophytic infection is onychomycosis. The term "onychomycosis" includes, but is not limited to, distal lateral subungual, superficial white, proximal white subungual, secondary dystrophic, primary dystrophic, endonyx, candidal (e.g. onycholysis & chronic mucocutaneous disease) types of onychomycosis and *Tinea ungium.*

Non-dermatophytic fungi associated with onychomycosis include *Aspergillus* spp. *Cephalosporum* spp., *Fusarium oxysporum, Scopularis brevicaulis,* and *Scytalidium* spp.

The peptides of the invention are potent antimicrobial peptides for a wide variety of pathogenic organisms. However, the peptides of the invention may also be useful in the treatment of other conditions including, but not limited to, conditions associated with mucosal infections, for example, cystic fibrosis, gastrointestinal, urogenital, urinary (e.g kidney infection or cystitis) or respiratory infections.

The peptides of the invention may also be useful in the treatment or prevention of infections associated, typically with skin, including, inter alia, wounds, ulcers and lesions for example, cutaneous wounds such cuts or burns, and conditions associated therewith.

In a preferred aspect of the invention the peptides are useful in the treatment of bacterial skin infections or "pyodermas".

The term "treatment" relates to the effects of the peptides described herein that impart a benefit to patients afflicted with an (infectious) disease, including an improvement in the condition of the patient or delay in disease progression.

As used herein "treatment of a wound" may include wound healing and associated conditions and therapy which promotes, augments, or accelerates healing of tissues and includes post-operative scarring, burns, ulcers, psoriasis, acceleration of tissue remodeling, for example, post cosmetic surgery and organ transplantation.

Thus, in a further aspect of the invention there is provided a substrate to which a peptide of the invention is applied or attached. Preferably, the substrate is suitable for application to wounds or delivery to wound sites. Preferably, the substrate allows for the transfer of the peptides of the invention from the substrate to a wound bed to achieve their antibiotic effect. The substrate may be a dressing, for example, wound dressing. The dressing may comprise a fabric material or it may be a collagen-like material.

The peptides of the invention may also find application as/in a disinfectant. In this context, the peptide or pharmaceutical compositions of the invention may be applied, either alone or in combination with other disinfecting agents, to a surface to be treated. As used herein a "surface to be treated" may be a substrate as defined herein or a medical device.

In a further aspect, the invention provides a method of treating or preventing a microbial infection in a subject comprising administering to said subject a therapeutically effective amount of a peptide according to the invention.

In a preferred method of the invention, the microbial infection is a fungal infection. In the method of the invention the peptide is applied topically to the skin or nails of said subject.

Mammals, birds and other animals may be treated by the peptides, compositions or methods described herein. Such mammals and birds include humans, dogs, cats and livestock, such as horses, cattle, sheep, goats, chickens and turkeys and the like. Moreover, plants may also be treated by the peptides, compositions or methods of the invention.

Where the subject is an animal, the method of the invention may be applied to nail-like features, including, but not exclusive to, hooves, claws and trotters.

The method of the invention may include, in addition to peptide treatment, treatments that enhance peptide permeation into the nail. This could be facilitated by chemical or physical means. Physical treatments, such as nail etching or filing of the dorsal layer of the nail may enhance permeability of the peptides of the invention. Chemical enhancement of nail permeability to the peptides of the invention may be achieved by breaking physical or chemical bonds within the nail plate keratin. Nail softening agents, including, but not exclusive to, urea and salicylic acid, increase hydration of the nail to decrease nail density and, therefore, may increase permeability to the peptides of the invention. Compounds containing sulfhydryl groups will cleave the disulfide bonds in nail keratin, and may lead to destabilization and increased permeability of drugs.

In a further aspect, the invention provides a method of treating a wound in a subject comprising applying to the wound a therapeutically effective amount of a peptide, or a substrate, according to the invention.

To achieve the desired effect(s), the peptide, a variant thereof or a combination thereof, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight or at least about 1 mg/kg to about 20 mg/kg of body weight, although other dosages may provide beneficial results. The amount administered will vary depending on various factors including, but not limited to, the peptide chosen and its clinical effects, the disease, the weight, the physical condition, the health, the age of the mammal, whether prevention or treatment is to be achieved, and if the peptide is chemically modified.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the peptides of the invention may be essentially continuous over a pre-selected period of time or may be in a series of spaced doses. Both local and systemic administration is contemplated.

To prepare the composition, peptides are synthesized or otherwise obtained, purified as necessary or desired, and then lyophilized and stabilized. The peptide can then be adjusted to the appropriate concentration and optionally combined with other agents. The absolute weight of a given peptide included in a unit dose can vary widely. For example, about 0.01 to about 2 g or about 0.01 to about 500 mg, of at least one peptide of the invention, or a plurality of peptides specific for a particular cell type can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Thus, one or more suitable unit dosage forms comprising the therapeutic peptides of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic peptides may also be formulated in a lipid formulation or for sustained release (for example, using microencapsulation, see WO 94/07529, and U.S. Pat. No. 4,962,091). The formulations may, where appropriate, be conveniently presented in discrete unit dosage forms and may be prepared by any of the methods well-known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic peptides of the invention are prepared for oral administration, they are generally combined with a pharmaceutically acceptable carrier, diluent or excipient to form a pharmaceutical formulation, or unit dosage form. For oral administration, the peptides may be present in a powder, a granular formation, a solution, a suspension, an emulsion or in a natural or synthetic polymer or resin for ingestion of the active ingredients from a chewing gum. The active peptides may also be presented as a bolus, electuary or paste. Orally administered therapeutic peptides of the invention can also be formulated for sustained release, e.g., the peptides can be coated, micro-encapsulated, or otherwise placed within a sustained delivery device. The total active ingredients in such formulations comprise from 0.1 to 99.9% by weight of the formulation.

Pharmaceutical formulations containing the therapeutic peptides of the invention can be prepared by procedures known in the art using well-known and readily available ingredients. For example, the peptide can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatine, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the peptides of the invention can include buffering agents such as calcium carbonate, magnesium oxide and magnesium carbonate. Suitable buffering agents may also include acetic acid in a salt, citric acid in a salt, boric acid in a salt and phosphoric acid in a salt. Caplets and tablets can also include inactive ingredients such as cellulose, pregelatinized starch, silicon dioxide, hydroxyl propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one peptide of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more peptides of the invention are designed to resist disintegration in the stomach and dissolve in the more neutral to alkaline environment of the duodenum.

The therapeutic peptides of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic peptides of the invention can also take the form of an aqueous or anhydrous solution or dispersion, or alternatively the form of an emulsion or suspension or salve.

Thus, the therapeutic peptides may be formulated for parenteral administration (e.g. by injection, for example, bolus injection or continuous infusion) and may be presented in unit dose form in ampules, pre-filled syringes, small volume infusion containers or in multi-dose containers. The active peptides and other ingredients may form suspensions, solutions, or emulsions in oily or aqueous vehicles, and may contain formulatory agents such as suspending, stabilizing and/or dispersing agents. Alternatively, the active peptides and other ingredients may be in powder form, obtained by aseptic isolation of sterile solid or by lyophilization from solution for constitution with a suitable vehicle, e.g., sterile, pyrogen-free water before use.

These formulations can contain pharmaceutically acceptable carriers, vehicles and adjuvants that are well-known in the art. It is possible, for example, to prepare solutions using one or more organic solvent(s) that is/are acceptable from the physiological standpoint, chosen, in addition to water, from solvents such as acetone, acetic acid, ethanol, isopropyl alcohol, dimethyl sulfoxide, glycol ethers such as the products sold under the name "Dowanol", polyglycols and polyethylene glycols, $C_1$-$C_4$ alkyl esters of short-chain acids, ethyl or isopropyl lactate, fatty acid triglycerides such as the products marketed under the name "Miglyol", isopropyl mytrisate, animal, mineral and vegetable oils and polysiloxanes.

Solvents or diluents comprising the peptides of the invention may include acid solutions, dimethylsulfone, N-(2-mercaptopropionyl) glycine, 2-n-nonyl-1,3-dioxolane and ethyl alcohol. Preferably the solvent/diluent is an acidic solvent, for example, acetic acid, citric acid, boric acid, lactic acid, propionic acid, phosphoric acid, benzoic acid, butyric acid, malic acid, malonic acid, oxalic acid, succinic acid or tartaric acid.

Also contemplated are combination products that include one or more peptides of the present invention and one or more other antimicrobial or antifungal agents, for example, polyenes such as amphotericin B, amphotericin B lipid complex (ABCD), liposomal amphotericin B (L-AMB), and liposomal nystatin, azoles and triazoles such as voriconazole, fluconazole, ketoconazole, itraconazole, pozaconazole and the like; glucan synthase inhibitors such as caspofungin, micafungin (FK463), and V-echinocandin (LY303366); griseofulvin; allylamines such as terbinafine; flucytosine or other antifungal agents, including those described herein. In addition, it is contemplated that the peptides might be combined with topical antifungal agents such as ciclopirox olamine, haloprogin, tolnaftate, undecylenate, topical nysatin, amorolfine, butenafine, naftifine, terbinafine, and other topical agents.

Additionally, the peptides may be formulated as sustained release dosage forms and the like. The formulations can be so constituted that they release the active peptide, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g. stents, catheters, peritoneal dialysis tubing, draining devices and the like.

For topical administration, the active agents may be formulated as is known in the art for direct application to a target area. Forms chiefly conditioned for topical application take the form, for example, of creams, milks, gels, powders, dispersion or microemulsions, lotions thickened to a greater or lesser extent, impregnated pads, ointments or sticks, aerosol formulations (e.g. sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic peptides of the invention can be delivered via patches or bandages for dermal administration. Alternatively, the peptide can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Topical administration may be in the form of a nail coating or lacquer. For example, the antifungal peptides can be formulated in a solution for topical administration that contains ethyl acetate (NF), isopropyl alcohol (USP), and butyl monoester of poly[methylvinyl ether/maleic acid] in isopropyl alcohol.

Pharmaceutical formulations for topical administration may comprise, for example, a physiologically acceptable buffered saline solution containing between about 0.001 mg/ml and about 100 mg/ml, for example between 0.1 mg/ml and 10 mg/ml, of one or more of the peptides of the present invention specific for the indication or disease to be treated.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active peptides can also be delivered via iontophoresis, e.g., as disclosed in U.S. Pat. Nos. 4,140,122; 4,383,529; or 4,051,842. The percentage by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic peptides in an aqueous or non-aqueous base also comprising one or more dispersing agents, solubilizing agents or suspending agents. Liquid sprays can be pumped, or are conveniently delivered from pressurized packs. Drops can be delivered via a simple eye dropper-capped bottle, via a plastic bottle adapted to deliver liquid contents drop-wise, or via a specially shaped closure.

The therapeutic peptide may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

Specific non-limiting examples of the carriers and/or diluents that are useful in the pharmaceutical formulations of the present invention include water and physiologically acceptable buffered saline solutions such as phosphate buffered saline solutions pH 7.0-8.0.

The peptides of the invention can also be administered to the respiratory tract. For administration by inhalation or insufflation, the composition may take the form of a dry powder, for example, a powder mix of the therapeutic agent and a suitable powder base such as lactose or starch. Therapeutic peptides of the present invention can also be administered in an aqueous solution when administered in an aerosol or inhaled form. Thus, other aerosol pharmaceutical formulations may comprise, for example, a physiologically acceptable buffered saline solution containing between about 0.001 mg/ml and about 100 mg/ml for example between 0.1 and 100 mg/ml, such as 0.5-50 mg/ml, 0.5-20 mg/ml, 0.5-10 mg/ml, 0.5-5 mg/ml or 1-5 mg/ml of one or more of the peptides of the present invention specific for the indication or disease to be treated.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

EXAMPLES

Materials and Methods

Example 1

Cyclization of a 7 amino acid polylysine peptide was performed by dissolving 1 eq of protected peptide with 1 eq (eq=equivalent volume) of HATU in DMF (dimethylformamide) at 100 mg/ml. To increase the pH 2.5 eq of DIEA (diisopropylethylamine) were added and the progress of the reaction followed by HPLC. When complete the peptide was precipitated in water and washed in further water. The peptide was then dried and de-protected with hydrofluoric acid in order to produce the final cyclic peptide. Ion-exchange chromatography is then used to replace the hydrofluoric acid solvent with acetic acid prior to lyophilization.

Example 2

Cyclization of a 7 amino acid polyarginine peptide was performed by combining 1 eq of protected peptide with 5 eq of $NaHCO_3$ (sodium bicarbonate) and 2 eq of PyBOP dissolved in DMF at 28.5 mg/ml. The reaction was followed by TLC and when complete the peptide was precipitated in water and washed in further water. The peptide was then dried and de-protected with hydrofluoric acid in order to produce the final cyclic peptide. Ion-exchange chromatography is then used to replace the hydrofluoric acid solvent with acetic acid prior to lyophilization.

Example 3

Cyclization of a 7 amino acid polyarginine peptide:
Solution 1: 57 mg of HBTU (Mwt=379.3, 0.15 mmole) or 57 mg of HATU (M=380.3, 0.15 mmole) and 60 µl of 0.92 mg/ml NMM (n-methylmorpholine, Mwt=101.2, 0.55 mmole) were dissolved in 2.86 ml of DMF.

Solution 2: 288 mg of H-[Arg(Pbf)]$_7$-OH (Mwt=2877.6, 0.1 mmole) (7 amino acid polyarginine peptide) were dissolved in 0.71 ml of DMF.

Solution 2 was added dropwise to solution 1 over 30 min. The pH was checked by wet pH paper and must be 8.5-9. The reaction mixture was stirred at room temperature overnight*. The mixture was concentrated under vacuum. A solution of NaHCO3 (5%) was added. The precipitate of protected cyclopeptide was filtered and washed with water. 150-200 mg was obtained. The cleavage of Pbf groups were performed in TFA/Water (95/5, v/v) (10 ml for 1 g of protected cyclopeptide). The mixture was concentrated and IPE was added to precipitate the crude product. 100-110 mg of crude cycloArg was obtained.

(*The coupling using HATU was complete after 5 hours. Quantity of NMM depend to excess of TFA in H-[Arg(Pbf)]$_7$-OH.)

The cyclic peptides are synthesized to be at least 95% enantiomerically pure, and tend to vary between 97 and 99%. They are at least 95% enantiomerically pure as synthesized by this method.

Broth Dilution Antifungal Susceptibility Testing

The sensitivity of relevant fungal strains to the cyclized peptides was determined using Clinical Laboratory Standard Institute (CLSI; formerly NCCLS) Approved Standards. Fungal susceptibility was tested using "Reference Method for Broth Dilution Antifungal Susceptibility Testing of Filamentous Fungi; Approved Standard M38-P", and yeast susceptibility was tested using "Reference Method for Broth Dilution Antifungal Susceptibility Testing of Yeasts; Approved Standard—Second Edition M27-A".

Broth Dilution Antibacterial Susceptibility Testing

The sensitivity of relevant bacterial strains to the cyclized peptides was determined using Clinical Laboratory Standard Institute (CLSI; formerly NCCLS) Approved Standards. Bacterial susceptibility was tested using "Methods for Dilution Antimicrobial Susceptibility Tests for Bacteria That Grow Anaerobically; Approved Standard—Seventh Edition M7-A7"

Haemolysis Assays

The peptide under study was aliquoted at the desired concentration in triplicate in Nunc 96 well plates, and serial 1:1 dilutions (100 µl) were made. 100 µl of washed (3 washes of 50 ml HBSS) pooled human red blood cells (RBC) ($1\times10^8$ RBC/ml) were added to the test wells and incubated at 37° C. for 3 hours. After incubation a further 100 µl of HBSS was added to all the wells and the plate was incubated at 4° C. overnight. 100 µl of the supernatant was removed and placed in a fresh microtitre plate which was read in a Sunrise plate reader (Tascam) at 450/620 nm. Control wells (quadruplicate) of buffer alone, buffer and RBCs, and $H_2O$ and RBC were also included. The data were plotted and statistically analyzed using Graph Pad (Prism software).

Results

Sequence of Cyclized Peptides

The sequence of the peptides analyzed is as follows:
Peptide 1: Cyclic-K-K-K-K-K-K-K
Peptide 2: Cyclic-R-R-R-R-R-R-R
Peptide 3: Cyclic-K-K-K-K-K-K-K-G
Peptide 4: Cyclic-R-R-R-R-R-R-R-G
Peptide 5: Cyclic-O-O-O-O-O-O-O-G
Peptide 6: Cyclic-dR-dR-dR-dR-dR-dR-dR-G
Peptide 7: Cyclic-dO-dO-dO-dO-dO-dO-dO-G
Peptide 8: Cyclic-dK-dK-dK-dK-dK-dK-dK-G The prefix 'D-' indicates a D-isomer of the amino acid was used in the synthesis of the peptide. 'O' represents the non-natural amino acid ornithine.

Cyclic peptides consisting of 3, 5, 9, 11, 13 or 15 arginine or lysine amino acids have been synthesized and activity has been determined (data not shown).

Antibacterial Activity of Cyclised Peptides

Cultures of *E. coli* and *Staphylococcus aureus* were exposed to Peptide 1 and the MIC after growth over the following 16 hours at 37° C. was 1 mM for both organisms (Table 2). Peptide 1 totally inhibits growth of both *E. coli* and *Staphylococcus aureus* at this concentration.

This experiment was repeated with Peptide 2. The MIC for Peptide 2 versus *E. coli* was 0.1 mM; The MIC for Peptide 2 versus *S. aureus* was 1.0 mM. This indicates a significant impact of the cyclized peptides on bacterial activity.

Linear peptides corresponding in size to peptides 1 and 2 demonstrated significantly lower activity than peptides 1 and 2 respectively.

Antifungal Activity of Cyclised Peptides Versus *Trichophyton rubrum*

*T. rubrum* susceptibility to peptides 1-8 was tested. Peptide 1 demonstrated an MIC of 0.1 mM versus cultures of *T. rubrum* (Table 2). Peptide 2 demonstrated an MIC of 0.25 mM versus cultures of *T. rubrum*.

Linear peptides corresponding in size to peptides 1 and 2 demonstrated significantly lower activity than peptides 1 and 2 respectively.

Peptides 3-8 had a single glycine residue introduced into the cyclic peptide ring. Thus, Peptides 3-8 are 8 amino acids in length, compared to 7 amino acids for Peptides 1-2. Peptides 3-6 all demonstrated antifungal activity against *T. rubrum* (MIC (mM) 4.0, 2.0, 4.0, 1.0, respectively). Peptides 7-8 did not demonstrate antifungal activity against *T. rubrum* at the maximum concentration tested (4 mM).

Peptides 3-6 demonstrate antifungal activity, but the introduction of the non-cationic amino acid glycine significantly reduces antifungal activity. For example, this can be seen in the activity of Peptide 2 (no Glycine; MIC=0.2 mM) compared with Peptide 4 (Glycine added; MIC=2.0 mM) (Table 2). This data shows that antifungal activity is present in cyclic peptides of both 7 and 8 amino acids in length, but that peptides of reduced cationicity are less antifungal towards *T. rubrum*.

Inhibition of *Trichophyton interdigitale* by Cyclised Peptides

*T. interdigitale* susceptibility to peptides 2-8 was tested. Antifungal activity of Peptides 2-8 against *T. interdigitale* is shown in Table 2. Peptides 2, 4 and 6 were active towards *T. interdigitale*.

Inhibition of *Cryptococcus neoformans* by Cyclised Peptides

*C. neoformans* susceptibility to peptides 4 and 6-8 was tested using "Reference Method for Broth Dilution Antifungal Susceptibility Testing of Yeasts; Approved Standard—Second Edition M27-A".

Table 2 demonstrates that cationic cyclic peptides 4 and 6-8 are antifungal versus the pathogenic yeast *C. neoformans* (MICs=1.0 mM, 0.5 mM, 2.0 mM and 0.5 mM, respectively).

Antimicrobial Activity of Peptide 2 Versus Selected Microbial Pathogens

The antimicrobial activity of Peptide 2 against 60 selected microbial pathogens is demonstrated in Table 3. As can be seen, greatest antimicrobial activity (i.e. lowest MICs) is consistently seen against fungi, especially dermatophytes, *Scopulariopsis brevicaulis*, *Malassezia furfur*, non-albicans *Candida* spp. and the bacterium *E. coli*.

Effect of the Use of Enantiomeric Amino Acids in the Cyclized Peptides

Comparison of the inhibitory effect of all-L and all-D cyclic cationic peptides is demonstrated in Table 2. Peptides 4 and 6 are all-L and all-D equivalent cyclic cationic peptides containing the amino acids arginine (7 aa) and glycine (1 aa). Antifungal activity against *T. rubrum* is greater for the all-D version than the all-L version (MIC=1.0 and 2.0 mM, respectively). Antifungal activity against *T. interdigitale* is greater for the all-D version than the all-L version (MIC=0.25 and 0.5 mM, respectively). Antifungal activity against the yeast *C. neoformans* is greater for the all-D version than the all-L version (MIC=0.5 and 1.0 mM, respectively). This indicates that the all-D version of this peptide is more active than the all-L version.

Peptides 3 and 8 are all-L and all-D equivalent cyclic cationic peptides containing the amino acids lysine (7 aa) and glycine (1 aa). Antifungal activity against *T. rubrum* is greater for the all-L version than the all-D version (MIC=4.0 and >4.0 mM, respectively). Neither peptide demonstrates antifungal activity against *T. interdigitale* (MIC>4.0 mM for both peptides).

Haemolytic Activity of Cyclized Peptides

The haemolytic activities of cyclic cationic peptides (Table 4) are negligible at concentrations in excess of those demonstrating antifungal activity.

Hepatotoxicity of Cyclized Peptides

Peptides 2, 9 and 10 show no hepatotoxicity at concentrations similar to those demonstrating antifungal activity.

TABLE 1

Coupling agents

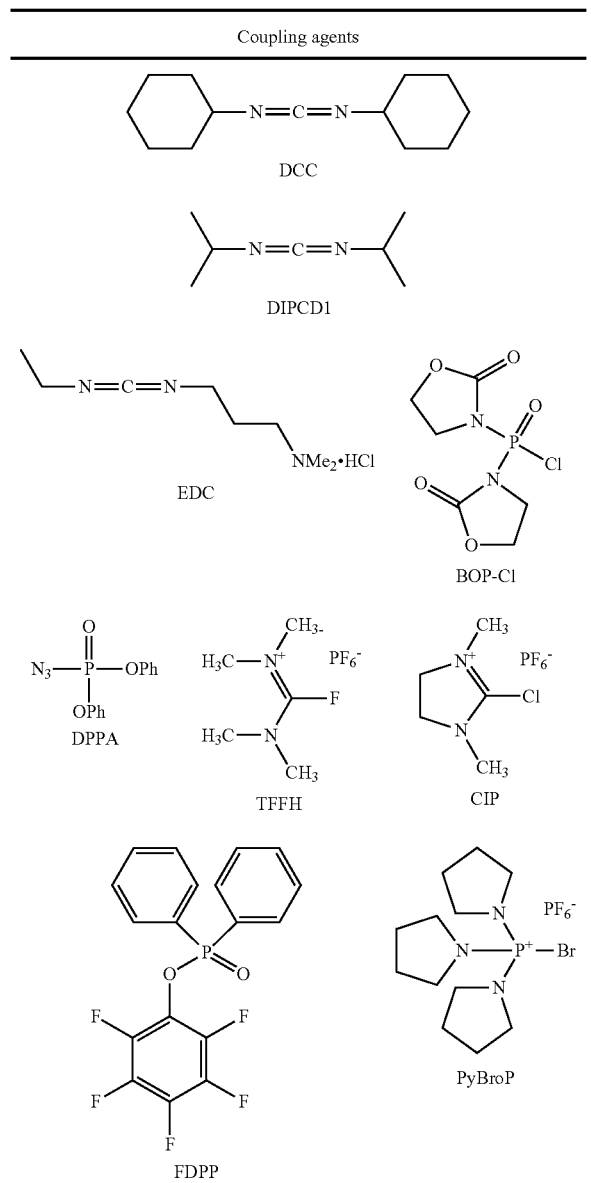

TABLE 1-continued

Coupling agents

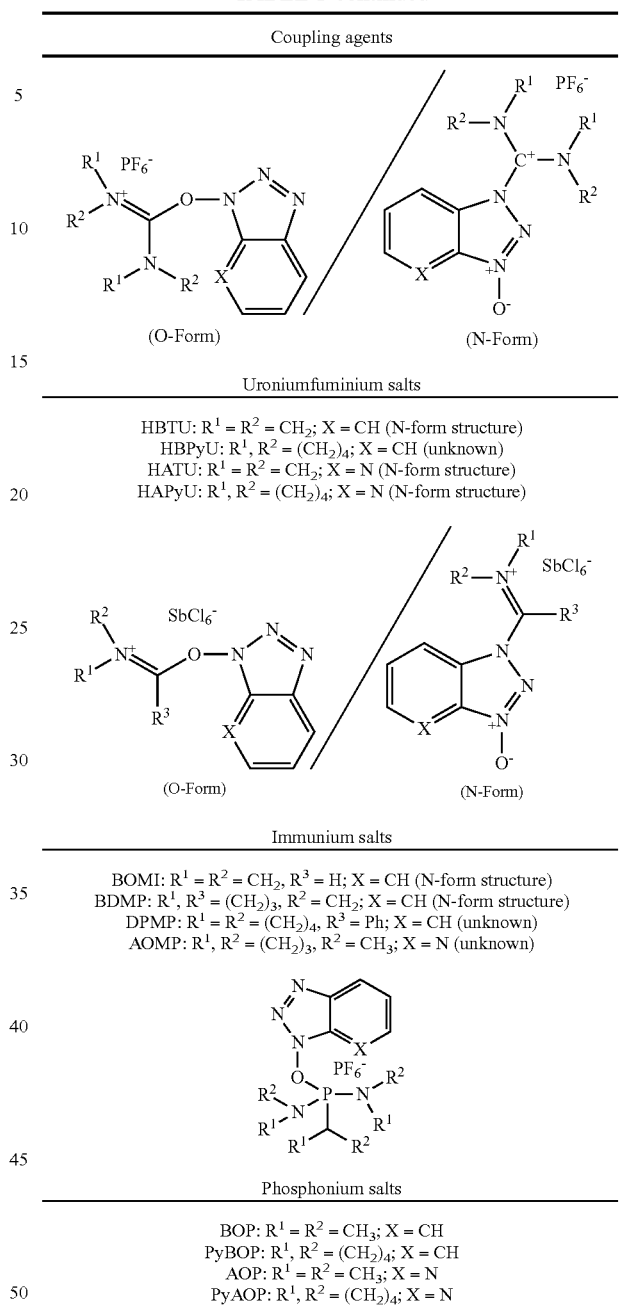

Uroniumfuminium salts

HBTU: $R^1 = R^2 = CH_2$; $X = CH$ (N-form structure)
HBPyU: $R^1, R^2 = (CH_2)_4$; $X = CH$ (unknown)
HATU: $R^1 = R^2 = CH_2$; $X = N$ (N-form structure)
HAPyU: $R^1, R^2 = (CH_2)_4$; $X = N$ (N-form structure)

Immunium salts

BOMI: $R^1 = R^2 = CH_2$, $R^3 = H$; $X = CH$ (N-form structure)
BDMP: $R^1, R^3 = (CH_2)_3$, $R^2 = CH_2$; $X = CH$ (N-form structure)
DPMP: $R^1 = R^2 = (CH_2)_4$, $R^3 = Ph$; $X = CH$ (unknown)
AOMP: $R^1, R^2 = (CH_2)_3$, $R^2 = CH_3$; $X = N$ (unknown)

Phosphonium salts

BOP: $R^1 = R^2 = CH_3$; $X = CH$
PyBOP: $R^1, R^2 = (CH_2)_4$; $X = CH$
AOP: $R^1 = R^2 = CH_3$; $X = N$
PyAOP: $R^1, R^2 = (CH_2)_4$; $X = N$

TABLE 2

Antimicrobial Activity (MIC; mM) of Cyclised Peptides versus Selected Microbial Pathogens

| Peptide | Molecular Weight (Da) | T. rubrum | T. interdigitale | E. coli | S. aureus | C. neoformans |
|---|---|---|---|---|---|---|
| 1 | 879.2 | 0.1 | ND | 1.0 | 1.0 | ND |
| 2 | 1093.3 | 0.25 | <0.125 | 0.1 | 0.25 | ND |
| 3 | 954.3 | 4.0 | >4.0 | ND | ND | ND |
| 4 | 1150.4 | 2.0 | 0.5 | ND | ND | 1.0 |
| 5 | 856.1 | 4.0 | >4.0 | ND | ND | ND |

TABLE 2-continued

Antimicrobial Activity (MIC; mM) of Cyclised Peptides versus Selected Microbial Pathogens

| Peptide | Molecular Weight (Da) | T. rubrum | T. interdigitale | E. coli | S. aureus | C. neoformans |
|---|---|---|---|---|---|---|
| 6 | 1150.4 | 1.0 | 0.25 | ND | ND | 0.5 |
| 7 | 856.1 | >4.0 | >4.0 | ND | ND | 2.0 |
| 8 | 954.3 | >4.0 | >4.0 | ND | ND | 0.5 |

TABLE 3

Antimicrobial Activity (MIC; mM) of Peptide 2 versus Selected Microbial Pathogens

| | Number | MIC (mM) |
|---|---|---|
| Fungus | | |
| T. rubrum | NCPF118 | 0.25 |
| T. rubrum | 7 Clinical Isolates[2] | 0.5-1.0 |
| T. interdigitale | NCPF335 | <0.125 |
| T. mentagrophytes | DM2006 978 | 0.5 |
| T. mentagrophytes | DM2006 1023 | 0.5 |
| M. furfur | DSM6170 | 0.031 |
| S. brevicaulis | NCPF2177 | 0.5 |
| S. brevicaulis | DM2006 1025 | 0.5 |
| A. niger | NCPF2022 | 0.5 |
| A. terreus | NCPF2729 | >2 |
| Fusarium oxysporum | NCPF2722 | >2 |
| Fusarium spp | DM2006 294 | >2 |
| Fusarium spp | DM2006 495 | >2 |
| Fusarium spp | DM2006 1026 | >2 |
| C. albicans | NCTC3179 | >2 |
| C. albicans | ATCC24433 | >2 |
| C. albicans | ATCC90028 | >2 |
| C. albicans | AM2003-020 | >2 |
| C. albicans | IHEM3742 | >2 |
| C. albicans | s20122.073 | >2 |
| C. krusei | NCPT3953 | 0.128-0.256 |
| C. krusei | ATCC6258 | 0.125 |
| C. parapsilosis | ATCC22019 | 0.25 |
| C. parapsilosis | ATCC90018 | 1.0 |
| Bacterium | | |
| S. aureus[1] | NCTC10442 | 0.25 |
| S. aureus[3] | NCTC6571 | >1.9 |
| S. aureus[2] | NCTC10788 | >1.9 |
| S. aureus[2] | ATCC12598 | 0.95 |
| S. aureus[2] | NCTC8325 | >1.9 |
| S. aureus[1] | Col | 0.95 |
| S. aureus[1] | N315 | 0.95 |
| S. aureus[1] | ANS46 | 0.95 |
| S. aureus[1] | MW2 | 0.95 |
| S. aureus | 16 Clinical Isolates[4] | >3.8 |
| Ps. aeruginosa | ATCC27853 | >1.9 |
| Ps. aeruginosa | DSM50071 | >2 |
| Ps. aeruginosa | ATCC27853 | >2 |
| B. cepacia | ATCC25609 | >1.9 |
| E. coli | NCTC12900 | 0.1 |
| S. aureus | ATCC25923 | >0.1 |
| P. acnes | DSMZ1897 | 0.125 |
| S. epidermidis | ATCC12228 | 0.025 |
| C. difficile | NCTC11209 | >2 |
| E. coli | No strain designation | 0.1 |
| S. aureus | No strain designation | 0.25 |

[1]MRSA (Methicillin-resistant S. aureus)
[2]Reference Numbers: DM2006 517; DM2006 902; DM2006 932; DM2006 953; DM2006 1008; DM2006 1093; DM2006 1377
[3]MSSA (Methicillin-sensitive S. aureus)
[4]Reference Numbers: 97.2935.K; 98.1695.K; 97.2637.D; 98.2028.X; 05.5240.R; 00.9523.R; 03.8996.T; 98.1515.F; 00.5472.R; 00.1039.P; 02.6225.E; 03.3200.J; 01.7995.S; 03.8951.G; 00.9521.M; 97.1636.D

TABLE 4

Haemolytic Activity of Selected Peptides versus Red Blood Cells

| Peptide | Maximum Concentration Tested (mM) | Haemolysis |
|---|---|---|
| 1 | | |
| 2 | 73.7 | None |
| 3 | 10.0 | None |
| 4 | 10.0 | None |
| 5 | 10.0 | None |
| 6 | 5.0 | None |
| 7 | 10.0 | None |
| 8 | 10.0 | None |

The invention claimed is:

1. A method of treating a bacterial infection in a subject, comprising administering to the subject a therapeutically effective amount of a composition of comprising a cyclic peptide and a pharmaceutically acceptable carrier, excipient or diluent, wherein the cyclic peptide comprises from 5 to 13 contiguous arginine residues and the bacterial infection is selected from the group consisting of: *Propionibacterium* spp.; and *Clostridia* spp.

2. The method of claim 1, wherein the arginine residues are D-amino acids.

3. The method of claim 1, wherein the arginine residues are L-amino acids.

4. A method of treating a bacterial infection in a subject, comprising administering to the subject a therapeutically effective amount of a composition comprising a cyclic peptide and a pharmaceutically acceptable carrier, excipient or diluent, wherein the cyclic peptide comprises 7 contiguous arginine residues and the bacterial infection is selected from the group consisting of: *Propionibacterium* spp.; and *Clostridia* spp.

5. The method of claim 4, wherein the bacterial infection is selected from the group consisting of: *Clostridium difficile*; and *Propionibacterium acnes*.

6. The method of claim 4, wherein the arginine residues are D-amino acids.

7. The method of claim 4, wherein the arginine residues are L-amino acids.

8. The method of claim 4, wherein the composition is administered topically.

9. The method of claim 1, wherein the bacterial infection is selected from the group consisting of *Clostridium difficile*; and *Propionibacterium acnes*.

10. The method of claim 1, wherein the composition is administered topically.

* * * * *